United States Patent
Vresilovic et al.

(10) Patent No.: US 8,118,874 B2
(45) Date of Patent: Feb. 21, 2012

(54) REPLACEMENT OR SUPPLEMENTATION OF A NUCLEUS PULPOSUS USING A HYDROGEL

(75) Inventors: Edward Vresilovic, Ardmore, PA (US); Michael F. Keane, Downingtown, PA (US); Alastair J. T. Clemow, Princeton, NJ (US); Nigel G. Smith, Norwich (GB)

(73) Assignee: Synthes USA, LLC, West Chester, PA (US)

( * ) Notice: Subject to any disclaimer, the term of this patent is extended or adjusted under 35 U.S.C. 154(b) by 323 days.

(21) Appl. No.: 12/568,577

(22) Filed: Sep. 28, 2009

(65) Prior Publication Data

US 2010/0016907 A1 Jan. 21, 2010

Related U.S. Application Data

(62) Division of application No. 11/134,309, filed on May 23, 2005, now abandoned.

(60) Provisional application No. 60/572,764, filed on May 21, 2004.

(51) Int. Cl.
*A61F 2/44* (2006.01)
(52) U.S. Cl. .................................... 623/17.16
(58) Field of Classification Search .... 623/17.11–17.16; 606/246, 279; 604/27, 28
See application file for complete search history.

(56) References Cited

U.S. PATENT DOCUMENTS

| | | | |
|---|---|---|---|
| 2,301,716 A * | 11/1942 | Sundstrand | 400/34 |
| 4,911,718 A * | 3/1990 | Lee et al. | 623/17.15 |
| 5,545,229 A * | 8/1996 | Parsons et al. | 623/17.15 |
| 5,976,186 A | 11/1999 | Bao et al. | |
| 6,231,715 B1 * | 5/2001 | Schleinz et al. | 156/277 |
| 6,231,716 B1 * | 5/2001 | White et al. | 156/345.54 |
| 6,264,695 B1 | 7/2001 | Stoy | |
| 6,280,475 B1 * | 8/2001 | Bao et al. | 623/17.16 |
| 6,387,130 B1 * | 5/2002 | Stone et al. | 623/17.16 |
| 6,610,094 B2 * | 8/2003 | Husson | 623/17.16 |
| 6,620,196 B1 | 9/2003 | Trieu | |
| 7,070,809 B2 * | 7/2006 | Goupil et al. | 424/489 |
| 2003/0220695 A1 * | 11/2003 | Sevrain | 623/17.16 |
| 2004/0059418 A1 * | 3/2004 | McKay et al. | 623/17.16 |

(Continued)

FOREIGN PATENT DOCUMENTS

EP 0 700 671 3/1996

(Continued)

OTHER PUBLICATIONS

PCT International Search Report, issued on Nov. 2, 2005, for PCT Application No. PCT/US2005/018028.

(Continued)

*Primary Examiner* — Eduardo C Robert
*Assistant Examiner* — David Comstock
(74) *Attorney, Agent, or Firm* — Stradley Ronon Stevens & Young, LLP

(57) ABSTRACT

A nucleus pulposus of an intervertebral disc is supplemented or replaced by an elongated, physiologically fully hydrated hydrogel prosthesis inserted into the central region of an intervertebral disc, where it can fold upon itself to form a prosthesis body within the central region of the annulus fibrosus. The hydrogel prosthesis may have expanded portions that assist in preventing expulsion of the prosthesis through the insertion aperture. An instrument for inserting the prosthesis has a cutter for severing the elongated prosthesis within the central region of the intervertebral disc after a sufficient amount has been implanted.

20 Claims, 7 Drawing Sheets

U.S. PATENT DOCUMENTS

| | | | |
|---|---|---|---|
| 2004/0092653 A1 | 5/2004 | Ruberti et al. | |
| 2005/0055099 A1* | 3/2005 | Ku | 623/17.16 |
| 2005/0119750 A1* | 6/2005 | Studer | 623/17.16 |

FOREIGN PATENT DOCUMENTS

| | | |
|---|---|---|
| EP | 1 229 873 | 1/2004 |
| JP | 2003513685 | 4/2003 |
| WO | WO 02/085262 | 10/2002 |
| WO | WO 03/020169 | 3/2003 |
| WO | 2004026189 | 1/2004 |

OTHER PUBLICATIONS

PCT International Preliminary Report on Patentability, issued Nov. 21, 2006, for PCT Application No. PCT/US2005/018028.

Thomas, Jonathan et al. "The Effect of Dehydration History on PVA/PVP Hydrogels for Nucleus Pulposus Replacement" Journal of Biomedical Materials Research, vol. 69, No. 2, May 15, 2004, pp. 135-140.

Chinese Office Action, issued Apr. 24, 2009, for Chinese Patent Application No. 200580024263.5.

Aug. 22, 2011 JP Office Action.

Joshi, et al., The Effect of Hydrogel Nucleus Implant on the Mechanical Behavior of the Lumbar Functional Spinal Unit: An Experimental Study, Proc. of the IEEE Annual Conf., 2003, vol. 29, pp. 211-212.

Joshi, et al., The Effect of Nucleus Implant Modulus on the Mechanical Behavior of Lumbar Functional Spinal Unit: A Finite Element Study, Proc. of the IEEE Ann. Northeast Bioeng. Conf, 2003, vol. 29, pp. 176-177.

Thomas, et al., Novel Associated Hydrogels for Nucleus Pulposus Replacement, Journal of Biomedical Mat. Res., Part A, 2003, vol. 67, pp. 1329-1337.

Thomas, et al., The Effect of Dehydration History on PVA/PVP Hydrogels for Nucleus Pulposus Replacement, Journal of Biomedical Materials Biomaterials, 2004, vol. 69, pp. 135-140.

Thomas, The Effect of Fatigue on Associating Hydrogels for Nucleus Pulposus Replacement, Proc. of the IEEE Annual Conf., 2003, vol. 29, pp. 174-175.

* cited by examiner

Tensile Test

REPLACEMENT OR SUPPLEMENTATION OF A NUCLEUS PULPOSUS USING A HYDROGEL

CROSS REFERENCE TO RELATED APPLICATION

This application is a division of U.S. application Ser. No. 11/134,309, filed on May 23, 2005, now abandoned which claimed priority under 35 U.S.C. §119(e) to U.S. Provisional Application No. 60/572,764, filed May 21, 2004, all of which are incorporated by reference herein in their entirety.

FIELD OF THE INVENTION

The present invention relates to replacing or supplementing the natural nucleus pulposus of the intervertebral disc and more particularly to replacing or supplementing a nucleus pulposus using an elongated hydrogel implant.

BACKGROUND OF THE INVENTION

Chronic back pain, typically lower back pain, caused by injury or age-related degeneration of an intervertebral disc is a condition experienced by many patients.

Current treatment options for back pain range from conservative bed rest to highly invasive surgical procedures including spinal fusion and total disc replacement.

The human intervertebral disc is comprised of two major structures, an outer or peripheral tendinous structure, referred to as the annulus fibrosus or annulus, and an inner gelatinous nucleus pulposus located in a generally central region within the annulus fibrosus. Degeneration of the nucleus t typically associated with natural ageing, leads to disc degradation and loss of function. Consequently, another surgical option for the relief of back pain is replacement of the nucleus, leaving the annulus intact. The aim of nucleus replacement is to relieve pain, to restore healthy physiological function to the disc, and to prevent additional wear on the annulus.

In view of the gelatinous nature of the nucleus pulposus, the use of hydrogels to replace the natural nucleus pulposus has been proposed and materials and methods for such replacement have been proposed.

Hydrogels are typically formed from solid, generally insoluble hydrophilic polymers and, in their hydrated state, have a generally water-swollen structure. It has been proposed to design hydrogel implants that may have mechanical properties which approximate those of the natural nucleus pulposus, and to implant such hydrogel prostheses into the central region of an intervertebral disc, i.e., into the cavity normally occupied by the nucleus pulposus.

SUMMARY OF THE INVENTION

According to the invention, a nucleus pulposus of an intervertebral disc is supplemented or replaced by introducing into the central region of an annulus fibrosus a quantity of a biocompatible, physiologically fully hydrated hydrogel in the form of an elongated solid hydrogel body.

Accordingly, one aspect of the invention to provide a method of replacing or supplementing a nucleus pulposus of an intervertebral disc.

A further aspect of the invention is to supplement or replace a nucleus pulposus by introducing a substantially fully physiologically hydrated hydrogel into the central region of an intervertebral disc.

A further aspect of the invention is to introduce such a hydrogel into the central region of an intervertebral disc, wherein the hydrogel is introduced in the form of an elongated solid body having a ratio of length to maximum transverse dimension of not less than about 5:1.

A further aspect of the invention is to provide a nucleus pulposus prosthesis that utilizes a physiologically fully hydrated hydrogel that is compatible in terms of the equilibrium water exchange, e.g., isotonic or iso-osmotic" with the local tissues, i.e., nucleus pulposus and annulus fibrosus.

A further aspect of the invention is to provide a nucleus pulposus prosthesis wherein the hydration level is substantially independent of the applied loads encountered in the normal physiological load bearing of the intervertebral disc (i.e, about 150N to about 1500N), thereby providing a constant volume of hydrated hydrogel in situ.

A further aspect of the invention is to provide a physiologically substantially fully hydrated hydrogel that provides the clinician with improved control over implantation intra operatively.

Further aspects of the invention will become apparent from the description of the invention which follows and the accompanying drawings.

DETAILED DESCRIPTION OF THE INVENTION

Figure 1:
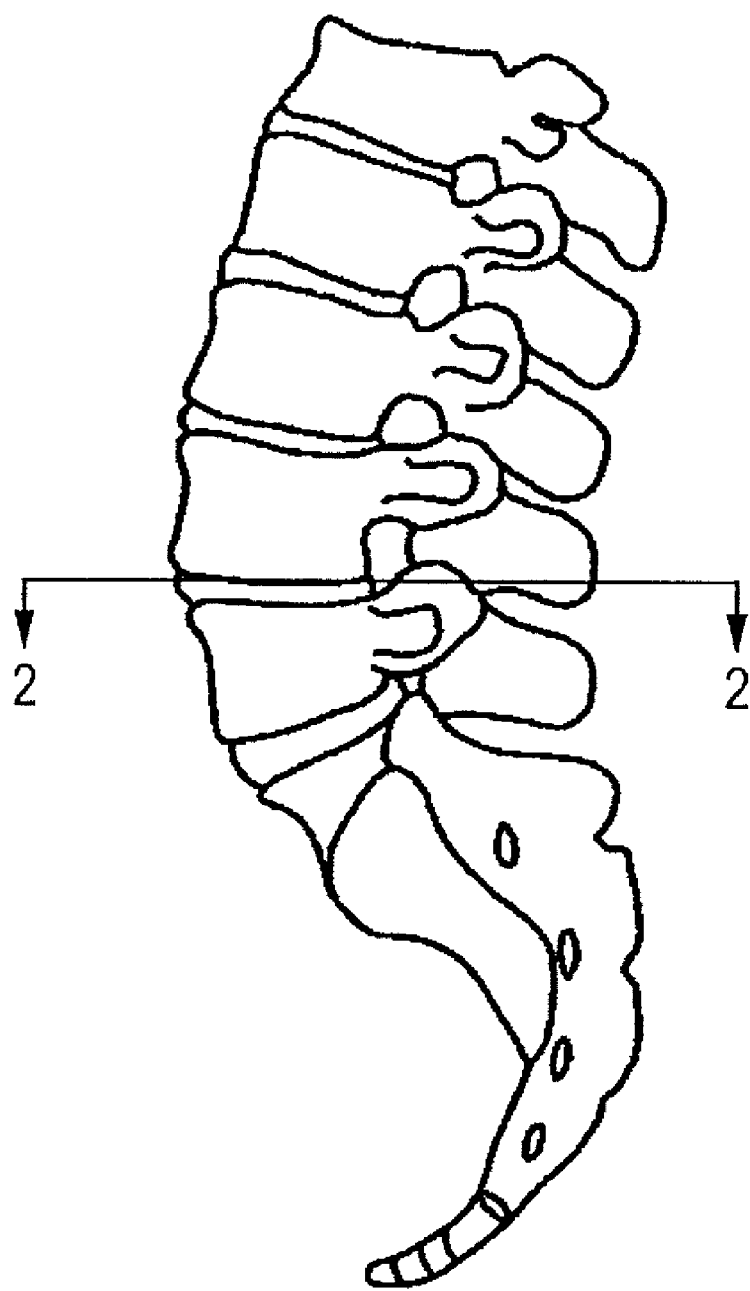
FIG. 1 is a schematic illustration of a portion of the human spinal column.

It is generally recognized that the volume of the normal human nucleus pulposus is about 5 cubic centimeters (cc). However, exact measurement is difficult, since the interface between the nucleus and surrounding annulus is frequently indistinct, particularly in more elderly patients. Although not normally measured, a typical nuclectomy procedure (often called a discectomy) involves the removal of between 0.1 and 2 cc of nucleus. The concept of nucleus replacement therefore contemplates insertion of a similar quantity of polymeric material in order to fully restore the normal function of the disc.

The present invention provides for replacing the amount of nucleus removed in a nuclectomy procedure, or for supplementing a nucleus pulposus that has become degenerated by reason of age, injury, or the like, with a relatively low-modulus hydrogel polymer. According to the invention, an implant which is relatively long and thin is inserted into the central cavity of an intervertebral disc through a narrow cannula. The prosthesis may be inserted through the annulus fibrosus or through the adjacent vertebral body and vertebral endplate. After entering the nucleus cavity, the thin implant may bend, fold upon itself, and become entangled so that it becomes compacted and acts like a single monolithic structure. While this method is suitable for most hydrogel materials, the present invention is primarily intended to employ high water content, low modulus (<4 MPa) polymers, since such polymers tend to conform readily to surrounding containing structures and therefore provide for an efficient and conforming filling of a nucleus cavity.

The present invention makes use of a hydrogel, preferably osmotically balanced (isotonic) with respect to the tissues in the intervertebral disc with which it comes into contact. Such a hydrogel will not take up water from nor release water into the surrounding tissue in any substantial amount and shall thus be referred to herein as a "physiologically fully hydrated hydrogel". Such a hydrogel will retain the degree of hydration that it had when implanted, and a prosthesis made from such a hydrogel will not experience any substantial change in its mechanical properties due to a change in degree of hydration after it has been implanted. Consequently, when a such a hydrogel in the form of an elongated relatively narrow body or string according to the invention is implanted by the procedure described herein, it will incrementally fill the available space in the nucleus pulposus cavity of an intervertebral disc until an amount has been implanted that will restore as much as possible the original natural function of the intervertebral disc, and, will not thereafter experience changes in mechanical properties. Such a hydrogel is typically relatively soft, i.e. has a relatively low modulus, and is therefore well adapted to conform to the cavity into which it is inserted and thereby pack and fill the cavity. Thus, complete filling of the cavity is achieved through essentially mechanical procedures at the time of implantation.

Additionally, the present invention reduces the risk of subsequent expulsion of the implant through either the hole in the annulus fibrosus or another hole or defect in the annulus fibrosus by providing certain embodiments of the implant provided with terminal portions having a cross-sectional area substantially larger than that of the main body of the implant. Alternatively or additionally, the implant may have such expanded portions located between the ends of the implant. Such a design provides additional security against expulsion of the implant out of the nucleus pulposus cavity.

The hydrated hydrogel may be inserted into a cavity formed within the central region of the annulus fibrosus by total or partial removal of the natural nucleus pulposus. Alternatively, the hydrogel material may be inserted into the nuclear cavity of an annulus fibrosus wherein no natural or artificial cavity has been created in order to supplement the natural nucleus pulposus in a patient whose natural nucleus pulposus has become degenerated or has at least partially escaped through a herniation or rupture in the annulus fibrosus. It is also according to the invention to introduce into the nuclear cavity of the annulus fibrosus, prior to insertion of the hydrogel material, a flexible containment vessel, bag, envelope, container, or the like, into which the hydrogel material is subsequently inserted. In this embodiment, the bag or container serves as an additional means for containing the hydrogel material within the nuclear cavity of the annulus fibrosus and preventing subsequent expulsion.

The hydrogels suitable for use in the method of the invention include any biocompatible hydrogel having an appropriate modulus as indicated above. Such hydrogels are well-known to those skilled in the art, and an appropriate hydrogel may be readily selected from among known hydrogels. Typical hydrogels suitable for use in the invention include copolymers of polyvinyl alcohol (PVA) and poly (vinylpyrrolidone) (PVP), copolymers of methyl methacrylate and vinyl pyrrolidone, poly (N-isopropylacrylamide) (PNIPAArn), and the like. Certain hydrogels are disclosed in U.S. Pat. No. 5,976,186 (Bao); U.S. Pat. No. 6,280,475 (Bao); U.S. Pat. No. 6,264,695 (Stoy); U.S. Pat. No. 6,620,196 (Trieu); European Patent EP1229873, and U.S. patent application No. among others, the entire disclosure of each of which is incorporated herein by reference.

The solid, physiologically fully hydrated hydrogel is, as indicated above, preferably osmotically balanced with respect to the surrounding tissues in the intervertebral disc. Such tissues are generally in osmotic equilibrium with the surrounding physiological fluids and may therefore be described as generally exhibiting an osmotic pressure equivalent to that of ordinary physiological fluids, i.e., being isotonic with respect to the surrounding physiological fluid. The hydrogel prosthesis is equilibrated with an isotonic solution before implantation, thereby achieving physiological full hydration as described above. Typically, the physiological fluids in the intervertebral space exhibit an osmotic pressure in the range of 0.1 to 0.3 megapascals under normal, moderate physical activity. The prosthesis is therefore preferably equilibrated with a solution having an osmotic pressure substantially within that range, e.g., about 0.2 megapascals. Any conventional biocompatible solution can be used. A preferable equilibrating medium is a substantially isotonic aqueous solution. Such solutions are well-known to those skilled in the art, and have an osmotic pressure substantially equal to that of the physiological fluids of the human body. Such an isotonic aqueous solution may contain any conventional solute that is compatible with the subsequent implantation of the prosthesis. A preferred solute is a relatively high molecular weight polymer that will not itself penetrate into the prosthesis in any substantial amount. Such water-soluble polymers as poly (ethylene glycol), dextran, and the like, are suitable solutes for preparation of the substantially isotonic aqueous solution used to equilibrate the hydrogel prosthesis. The formulation and preparation of isotonic aqueous solutions is well-known to those skilled in the art.

Accordingly, the invention contemplates a method of hydrating a hydrogel, comprising contacting said hydrogel with a substantially isotonic solution for a period of time sufficient to achieve a desired level of hydration, in particular an equilibrium level of hydration. The contact is preferably accomplished by immersing the hydrogel in the substantially isotonic solution. In a preferred method of hydrating a hydrogel according to the invention the substantially isotonic solution is an isotonic aqueous solution of dextran. Thus, the invention contemplates making as prosthesis by providing a biocompatible hydrogel in a form suitable for use as a prosthesis, and hydrating the hydrogel in accordance with the method of the invention described above, as well as a prosthesis so prepared.

The solid, substantially fully hydrated hydrogel is introduced into the central cavity of an annulus fibrosus in the form of a generally elongated solid body having a dimensional ratio of its length to its principal diameter or transverse dimension, i.e., a dimension generally at right angles to the length or longest dimension, of at least about 5:1. Preferably the dimensional ratio of length to principal transverse dimension is at least about 10:1, more preferably about 50:1, still more preferably at least about 100:1, and still more preferably at least about 500:1. The dimensional ratio of longest dimension to principal transverse dimension may be as great as 1000:1 or greater. A particularly preferred dimensional ratio of length to principal transverse dimension is about 350:1.

The hydrogel used in the method of the present invention will typically have an elastic modulus not greater than about 4 MPa. Typically, the elastic modulus of the fully saturated hydrogel will be between about 0.05 MPa and 4.0 MPa. Preferably, the elastic modulus and transverse dimension will be chosen such that the hydrogel body can fold easily upon insertion into the central cavity of the annulus in order to fill substantially the entire volume of the cavity. Accordingly, the elongated hydrogel body will typically have a principal transverse dimension not greater than about 10 mm, preferably not greater than about 5 mm and more preferably not greater than about 2.5 mm. The principal transverse dimension of the elongated body is not subject to any strict minimum. It may be chosen, for example, to provide a suitable folding pattern within the central cavity of the annulus fibrosus, to provide a suitable amount of hydrogel material within a convenient length, or for other reasons relevant to the implantation method of the invention. Typically, the principal transverse dimension of the hydrogel body will be at least about 0.5 mm or greater.

The length and transverse dimensions of the hydrogel body to be inserted into the nucleus pulposus cavity of the annulus fibrosus will be determined by the total volume of hydrogel material to be inserted into the cavity. Accordingly, the skilled practitioner can readily determine an appropriate length and transverse dimensions in a particular situation.

The transverse cross-section of the elongated hydrogel body may be any convenient shape. For example, the elongated hydrogel body may have a generally circular, elliptical, square, rectangular, crescent-shaped, or other transverse cross-sectional shape as may be convenient for insertion through a given aperture or required by the need to fold within a cavity of a particular size or shape.

The hydrogel body to be inserted into the nucleus pulposus cavity of the intervertebral disc may also be provided with a portion of larger transverse cross-section at one or both ends thereof, in order to prevent expulsion of the hydrogel body through the insertion aperture in the annulus fibrosus or adjacent vertebral endplate. For example, either or both ends of the elongated hydrogel body may be provided with a generally spherical termination having a diameter somewhat greater than the principal diameter, i.e. the diameter of the central or non-terminal portion of the elongated hydrogel body. Alternatively, one or both of the ends of the elongated hydrogel body may be provided with a flared shape or one or more transverse or angulated cross-members, forming aT-shape, Y-shape, Xshape, or the like. Examples of such prostheses are illustrated in the drawings and described below. The hydrogel body, and/or the terminal portion of greater transverse cross-sectional area may be deformed, constricted, compressed, or the like before insertion through the insertion cannula. After insertion, such a deformed or compressed hydrogel body will expand to provide a shape designed to prevent expulsion through the insertion hole in the annulus fibrosus. The prosthesis may be manufactured by extrusion or conventional molding procedures, such as compression molding, injection molding, and the like.

According to the invention, a hydrogel polymer prosthesis is provided having a generally elongated shape, preferably having a relatively low modulus and a transverse cross-sectional profile such that it can be compressed to be extruded through a cannula having an inside diameter not greater than about 5 millimeters. In certain embodiments, the insertion cannula may have an inside diameter of 3.5 millimeters. In a preferred embodiment of the invention, a relatively soft polymer hydrogel is provided in a long cylindrical shape such that its diameter is not greater than about 5 mm and its length is sufficient to provide a volume of hydrogel sufficient for replacing or supplementing a nucleus pulposus. Such a prosthesis may have a length as long as about 300-500 mm. If the implant is not too long for convenient manipulation, it may be provided to surgery within a generally rigid cannula (metal or plastic) with an outer diameter slightly larger than the diameter of the implant. Once the nucleus cavity has been prepared to the surgeon's satisfaction, the end of the cannula is gently inserted through the annulus into the disc cavity. Using a rod of diameter similar to that of the hydrogel implant, the implant is pushed out of the cannula and fills the cavity. This is continued until either the pressure required to continue is too high or the surgeon is satisfied that sufficient hydrogel has been inserted. At this point, the implant is cut to length and the cut end pushed into the nucleus cavity. Alternatively, the implant may be provided in a separate storage tube, which can be somewhat flexible for convenient manipulation. Such a storage tube may then be coupled to a rigid cannula that is inserted or to be inserted through the annulus fibrosus as described above. In this embodiment a source of fluid pressure may be coupled to the distal end of the storage tube in order to extrude the implant thorough the insertion cannula and into the nucleus pulposus region of the intervertebral disc. When a sufficient amount of the implant has been inserted, the implant may be cut to length and the remainder pushed into the nucleus cavity as described above. In either procedure, the implant may also be severed within the nucleus pulposus region using an insertion cannula provided with an appropriate cutter. An example of such an insertion cannula is described below.

An exemplary method of implantation of a physiologically fully hydrated hydrogel according to the invention is illustrated schematically in FIGS. 1-5.

FIG. 1 illustrates a left lateral schematic view of the lumbar portion of a human spine 100, showing the general configuration of the vertebrae 102 and intervertebral discs 104. Although the invention will be described with respect to a lumbar intervertebral disc, a skilled practitioner will understand that it may be practiced with respect to any of the intervertebral discs that have a similar structure, with appropriate modifications as may be required.

The implantation of a hydrogel prosthesis of the invention is illustrated in FIGS. 2-5, wherein the procedure is viewed from a superior view of a typical intervertebral disc as indicated by the line 2-2 in FIG. 1.

Figure 2:
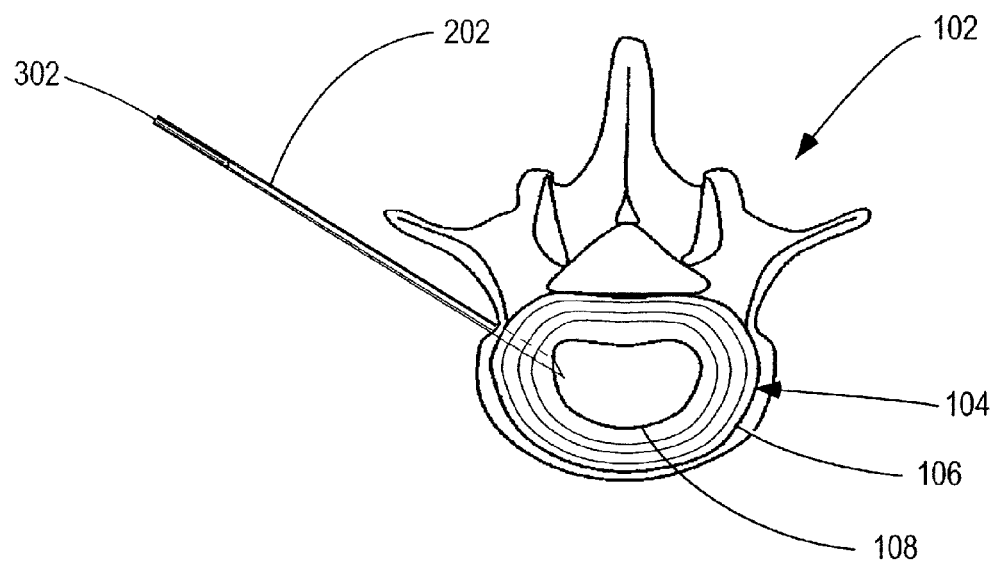
FIG. 2 schematically illustrates a first stage of implantation of a hydrogel material into a nucleus pulposus cavity according to the method of the invention, wherein a cannula through which the prosthesis is to be implanted has been inserted through the annulus fibrosus of the intervertebral disc.

FIG. 2 shows the initial step in the implantation of a hydrogel prosthesis of the invention wherein a cannula 202 has been inserted though the annulus fibrosus 106 of an intervertebral disc 104 and into the nucleus pulposus cavity 108. The nucleus pulposus cavity 108 may be in need of a prosthesis by reason of natural degeneration or leakage of the nucleus pulposus or after partial or total removal of the natural nucleus pulposus. The cannula 102 may be any type of conventional cannula, including a cannula having a sharp point as illustrated or a blunt point, inserted through the annulus fibrosus 106 by any conventional surgical technique. The cannula 202 is shown partly cut away to show a prosthesis of the invention 302 loaded within the cannula 202.

The length of the prosthesis will depend on the amount of hydrogel to be implanted, which in turn is dictated by the vacant volume in the nucleus pulpous cavity as may determined by conventional means. The length may be readily calculated from the cylindrical or other geometry of the prosthesis once the amount needed to fill the void space in the nucleus pulposus cavity, or to supplement the nucleus pulposus, has been determined. Alternatively, the prosthesis may be extruded into the cavity of the nucleus pulposus until the internal pressure reaches a value sufficient to restore, at least partially, the function of the intact nucleus pulposus.

The force required to extrude the hydrogel prosthesis in to the nucleus pulposus cavity may be supplied by any conventional means. If the amount of hydrogel to be implanted is relatively small/it may be contained in the rigid extrusion cannula and forced into the nucleus pulpous cavity with a stiff rod. Alternatively, a syringe or pump connected directly or indirectly to the external end of the implantation cannula may be used. If the amount of hydrogel to be implanted exceeds that which can be conveniently contained in a rigid implantation cannula, it may be supplied in a tube of appropriate size that is coupled to the external end of the implantation cannula and forced from the supply tube through the implantation cannula by any conventional means, such as described above.

Figure 3:
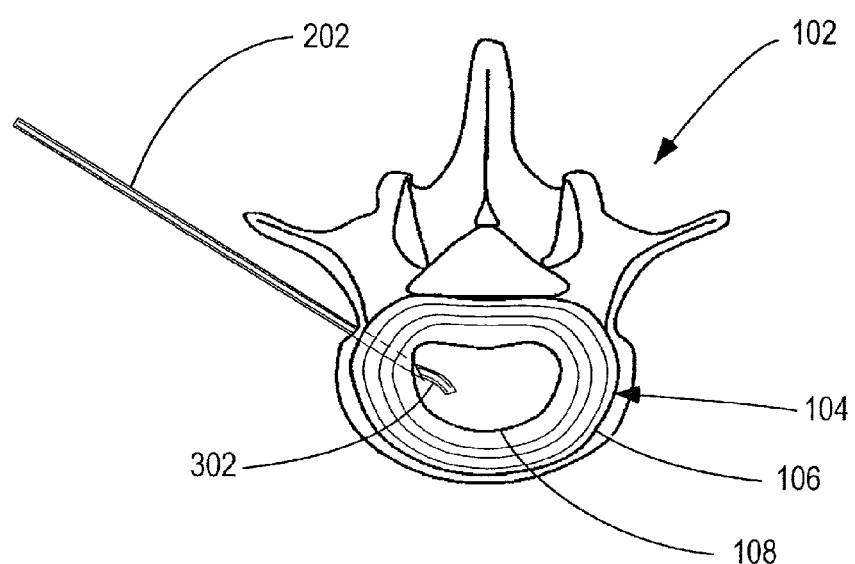
FIG. 3 schematically illustrates a second stage of the implantation, wherein extrusion of the hydrogel implant through the cannula into the cavity has begun.
Figure 4:
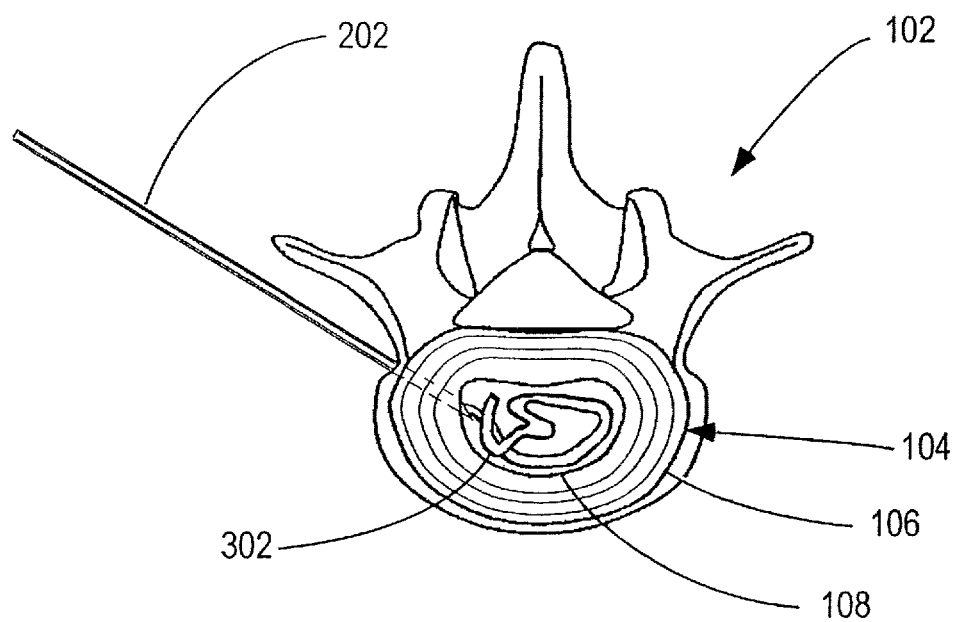
FIG. 4 schematically illustrates a third stage of the implantation wherein extrusion of the hydrogel implant continues.
Figure 5:
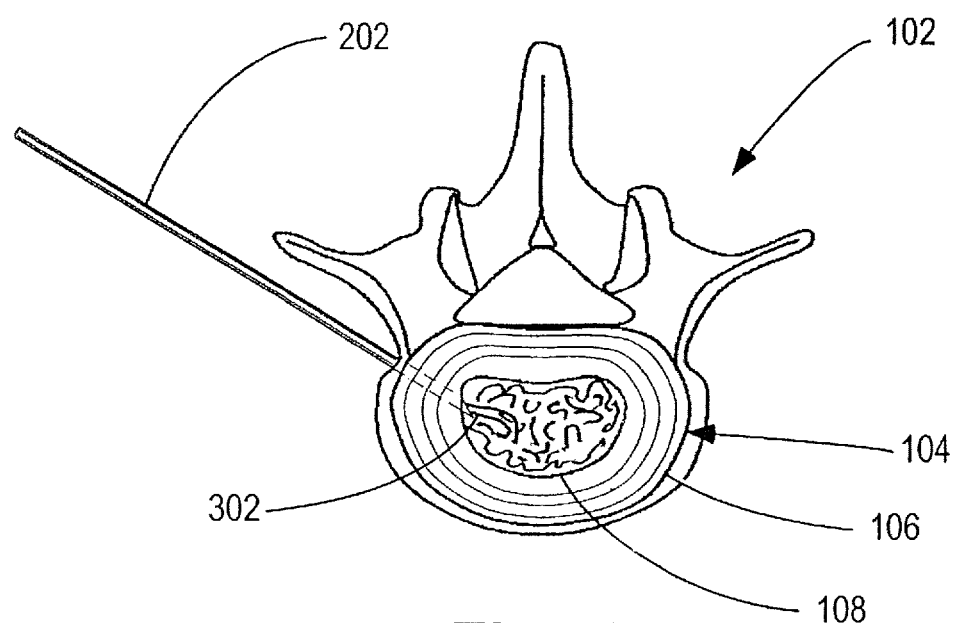
FIG. 5 schematically illustrates the final stage of the implantation wherein the cavity is substantially filled with hydrogel.

FIG. 3 shows an initial stage of the implantation wherein the extrusion of the implant from the cannula into the nucleus pulposus cavity has begun. FIG. 4 illustrates an intermediate stage in the implantation of the prosthesis wherein the prosthesis has begun to fill any vacant volume within the nucleus pulposus cavity and is folded upon itself as required to fit into the cavity. FIG. 5 illustrates the final stage of implantation wherein the prosthesis has substantially filled any vacant volume in the nucleus pulposus cavity and is preferably packed therein with sufficient pressure to approximate the pressure of the natural nucleus pulposus.

After the requisite amount of the hydrogel prosthesis has been extruded into the nucleus pulposus cavity, the terminal end is pushed into the cavity, for example by a rod passed through the cannula. Preferably, the terminal end of the prosthesis is moved to a position as far as readily possible from the hole through which the prosthesis was introduced. This procedure minimizes the possibility that an end of the prosthesis might find the hole and be expelled therethrough by the pressure present within the filled nucleus pulposus cavity.

In an alternative method of implanting the hydrogel prosthesis of the invention, the implant can be introduced into the nucleus cavity by passage through either the superior or inferior vertebral body. This approach has the advantage of not requiring any surgical procedure with respect to the annulus fibrosus/although it does require making an access aperture in the vertebral endplate. In this embodiment also, the relatively small diameter of the hydrogel prosthesis makes it possible to use a relatively small aperture in the vertebral endplate.

Figure 6:
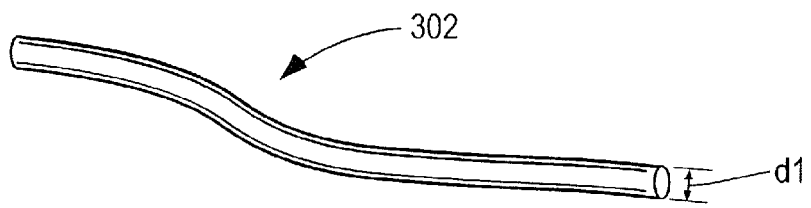
FIG. 6 illustrates an elongated generally cylindrical embodiment of the hydrogel implant of the invention.

FIG. 6 schematically illustrates a generally cylindrical prosthesis 302 as used in the method illustrated in FIGS. 2-5, having a principal diameter d1 typically not greater than about 5 millimeters. The length of such a prosthesis may vary, as indicated above, depending on the volume of hydrogel to be implanted into the nucleus pulposus cavity.

In order to decrease the probability that the hydrogel prosthesis of the invention will be expelled from the central region of the annulus fibrosus through the hole through which it was implanted, at least one portion, i.e., a portion of the length of the prosthesis, may have a cross-sectional area greater than that of another segment of the prosthesis. In particular, either or both ends of the prosthesis may be terminated in expanded portions, i.e., having a cross-sectional area greater than that of the central or non-terminal portion of the implant (principal cross-sectional area), as illustrated, e.g., in FIGS. 7 and 8, in order to reduce the probability of the prosthesis being expelled through the hole in the annulus fibrosus through which it was implanted. The end is typically compressed when the implant is inserted into the nuclear cavity in the annulus fibrosus and expands once inside the cavity.

Figure 7:
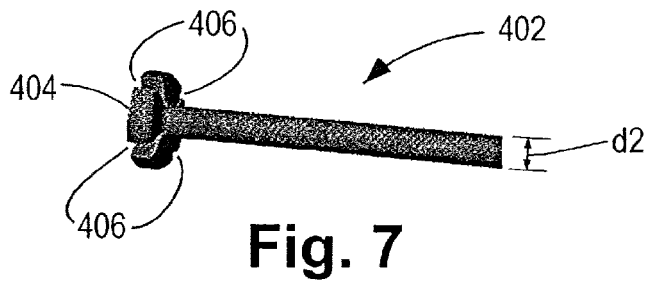
FIG. 7 illustrates a flare-ended embodiment of a hydrogel implant according to the invention.

Accordingly, FIG. 7 illustrates an alternative embodiment 402 of the prosthesis of the invention having a principal diameter d2 and a flared end 404 of greater diameter. Either end or both ends of the prosthesis may be flared in order to reduce the possibility of the prosthesis being expelled through the insertion hole made in the annulus fibrosus. The flared end 404 may be segmented circumferentially, as by the provision of circumferentially spaced cutouts 406, to facilitate deformation of the end for insertion into the nucleus pulposus cavity.

Figure 8:
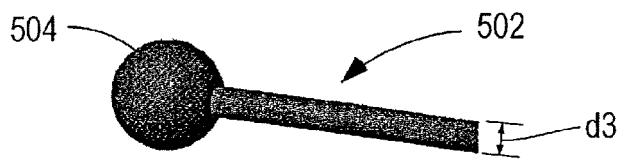
FIG. 8 illustrates a ball-ended embodiment of a hydrogel implant according to the invention.

FIG. 8 illustrates another embodiment 502 of the prosthesis of the invention having a principal diameter d3, wherein the elongated prosthesis is terminated with a generally spherical ball 504. Either or both ends of the prosthesis 502 may be terminated with a ball. The skilled practitioner will recognize that numerous alternative designs of expanded end portions of the prosthesis of the invention incorporating the same principle are possible.

Figure 9:
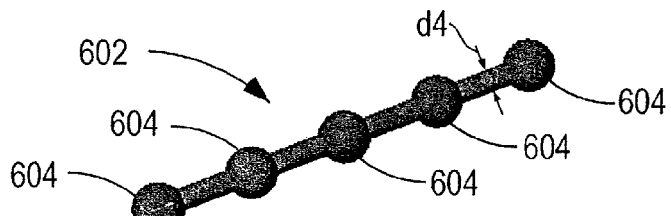
FIG. 9 illustrates an embodiment of the hydrogel prosthesis used in the method of the invention, wherein the prosthesis comprises an elongated structure having expanded portions in the form of beads positioned at intervals along the length of the prosthesis.
Figure 10:
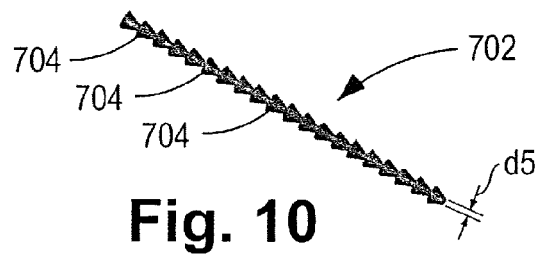
FIG. 10 illustrates an embodiment of the hydrogel implant according to the invention, wherein the prosthesis has directional barbs positioned along the length of the prosthesis.

In another embodiment of the prosthesis of the invention, the implant has one or more repeating structures having at least one transverse dimension greater than a principal transverse dimension (diameter d4) of the prosthesis. Such structures will have a cross-sectional area greater than that of the adjacent portions of the prosthesis. Preferably, at least one transverse dimension of such an expanded portion is greater than the diameter of the hole in the annulus fibrosus through which the introduction cannula was inserted. More preferably, the expanded portion is generally symmetrical about the axis of the prosthesis and has a transverse diameter greater than the diameter of the hole in the annulus fibrosus through which the introduction cannula is inserted. Two examples of such prostheses are illustrated in FIGS. 9 and 10. The skilled practitioner will recognize that numerous alternative designs incorporating the same principle are possible.

FIG. 9 shows a prosthesis 602 of principal diameter d4 having a number of generally spherical expanded portions (beads) 604 spaced along the prosthesis. The beads are typically compressed when the implant is inserted into the nuclear cavity in the annulus fibrosus and expand once the prosthesis has been inserted into the nucleus pulposus cavity.

FIG. 10 shows a prosthesis 702 of principal diameter or cross-dimension d5 having a number of barb-like projections 704 spaced along the prosthesis. The barbs may be located substantially contiguously along the body of the hydrogel prosthesis, or they may be spaced along the body of the prosthesis somewhat like the spherical expanded portions of the prosthesis illustrated in FIG. 9. The barbs are typically compressed when the implant is inserted into the nuclear cavity in the annulus fibrosus and expand once the prosthesis has been inserted into the nucleus pulposus cavity.

Figure 11:
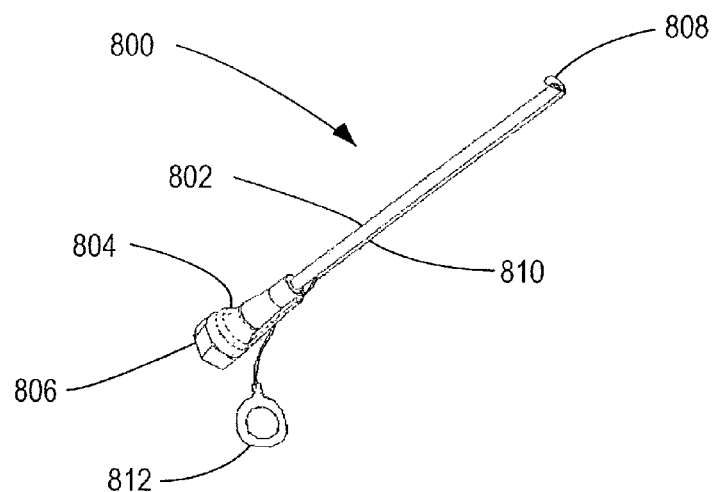
FIG. 11 illustrates an instrument for inserting an elongated hydrogel prosthesis according to the invention through an annulus fibrosus and into the central cavity of an intervertebral disc.

A suitable insertion instrument for inserting the hydrogel prosthesis of the invention into a nucleus pulpous cavity is illustrated in FIG. 11. The instrument 800 of FIG. 11 comprises a generally straight cannula portion 802, a funnel portion 804 and a coupling 806. In use, a prosthesis of the invention that is to be inserted in compressed form, e.g., a beaded prosthesis, such as illustrated in FIG. 9, is supplied contained within a tubular supply conduit which is coupled to the insertion instrument 800 via the coupling 806. The prosthesis is then forced from the supply conduit through the funnel portion 804 and through the straight portion 802 into the nucleus pulposus cavity. The insertion instrument 800 is also provided with a cutting wire loop 808 which is led through an auxiliary tube 810 attached to the straight portion 802 of the insertion instrument 800 to a handle or ring 812. When a sufficient amount of the hydrogel has been inserted into the nucleus cavity, the hydrogel can be severed inside the cavity by pulling on the handle 812, whereby the cutting loop 808 is tightened and cuts the prosthesis. The insertion instrument 800 is then withdrawn to complete the surgical implantation procedure.

Insertion of a compressible prosthesis using the insertion instrument 800 allows the implant to be inserted through a cannula which minimizes the hole in the annulus fibrosus, thus minimizing the trauma to the annulus, and also provides that the diameter of any passageway left in the annulus after the insertion cannula is withdrawn will be smaller than the diameter of the prosthesis that has been inserted. Such a minimized passageway will provide a further barrier to any possible expulsion of the prosthesis. The skilled practitioner will recognize that numerous alternative designs of an insertion cannula incorporating the same principle are possible.

The practice of the invention will be illustrated by the following nonlimiting examples.

EXAMPLE 1

This example illustrates the preparation of a preferred hydrogel used in the practice of the invention.

An amount of 12.7 g of PVA (Mowiol, supplied by Kuraray Co. Ltd., 132,000 $M_w$, 50,000 $M_n$, $P_D$ 2.6; >99.1% hydrolyzed) is mixed with 0.127 g of PVP (Plasdone, supplied by International Specialty Products, 58,000 $M_w$), 6.5 g of $BaSO_4$ and 81 mL of water. The solution is heated at 95° C. for 10 hrs and then placed into a mold. The mixture contained in the mold is then placed in a programmable environmental chamber and subjected to six successive freeze-thaw cycles ranging from +30° C. to −30° C. for 21 hours and 3 hours respectively. The gel so formed is then demolded and placed in a substantially isotonic osmotic aqueous solution of dextran for one day to osmotically balance the water content of the gel to a state similar to that of the human nucleus pulposus. Finally the prosthesis is packaged and sent for sterilization.

EXAMPLE 2

This example illustrates the basic mechanical properties of a hydrogel as prepared in Example 1.

Hydrogels often exhibit nonlinear mechanical properties and are highly deformable materials, and thus their properties are highly dependent on the testing and test conditions. A preferred hydrogel used in the invention was tested in the following manner to obtain the material incremental modulus. Tensile and compression properties were obtained as follows using a conventional mechanical testing machine.

Figure 12:
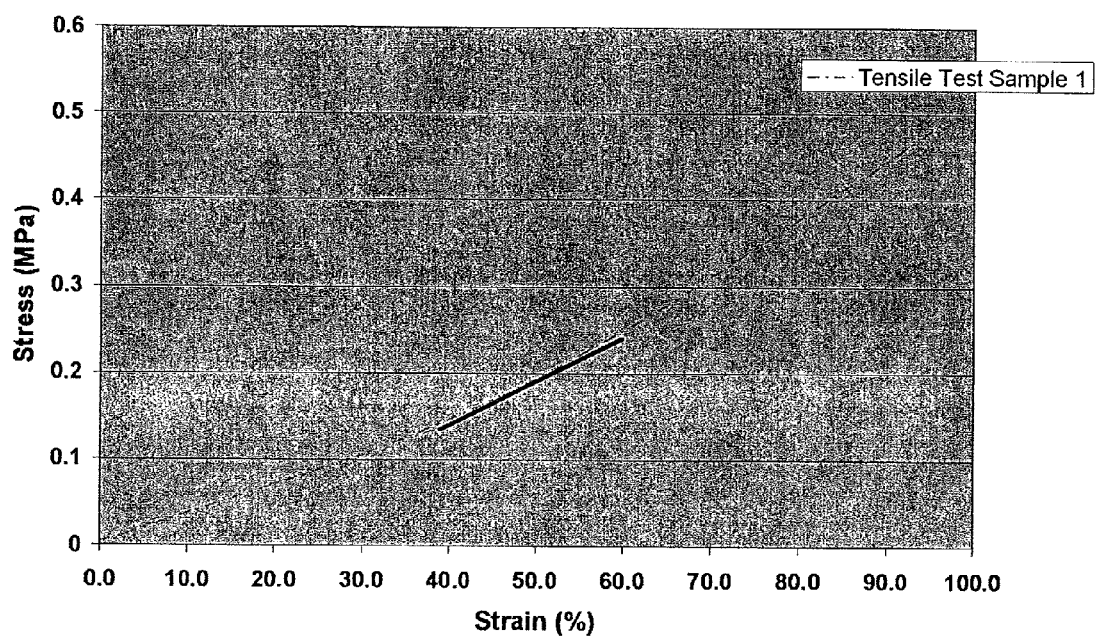
FIG. 12 illustrates the results of a representative test of the tensile properties of the hydrogel of the invention.

A tensile test is performed on a sample 3.8 mm in diameter and 100 mm in length of a hydrogel prepared as in Example 1. The sample is gripped on both ends such that a 60 mm hydrogel gauge length exists between each grip. A preload of 0.04N is applied to the specimen. A tensile test is then performed on the specimen at a rate of 60 mm/min. The incremental tensile modulus is calculated as the slope of the line passing through points corresponding to the representative strain level. FIG. 12 shows the output of a representative tensile test. A typical tensile modulus value of the preferred embodiment, tested as indicated above, is 0.675 MPa @ 50% strain.

Figure 13:
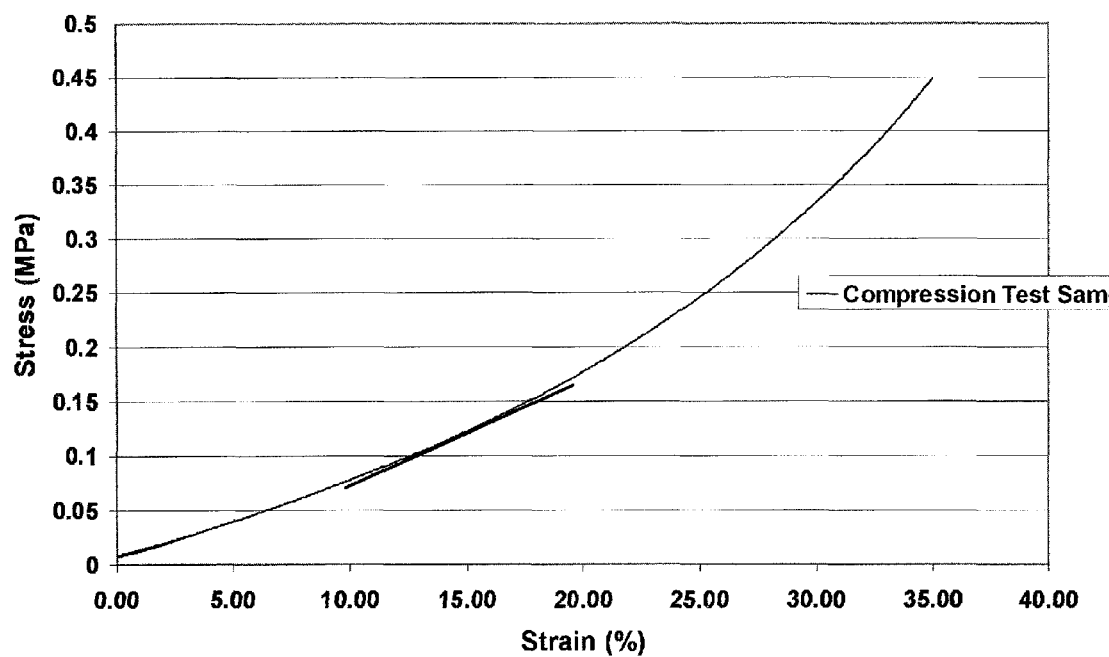
FIG. 13 illustrates the results of a representative test of the compression properties of the hydrogel of the invention.

A compression test is performed on a sample 12.0 mm in diameter and 8 mm in height of a hydrogel prepared as in Example 1. The sample is placed in a bath of a substantially iso-osmotic solution, e.g., a substantially isotonic aqueous solution of dextran, at 37° C. for testing. A compressive preload of 1N is applied to the specimen. A compression test is then performed on the specimen at a rate of 100% of test specimen height/min. The incremental compressive modulus is calculated as the slope of the line passing through points corresponding to the representative strain level. A plot of a typical compression test is presented in FIG. 13. A typical compressive modulus value of a preferred fully hydrated hydrogel of the invention is 0.984 MPa @ 15% strain.

EXAMPLE 3

This example illustrates the maintenance of the water content of the fully hydrated hydrogel of the invention under certain conditions of loading.

Figure 14:
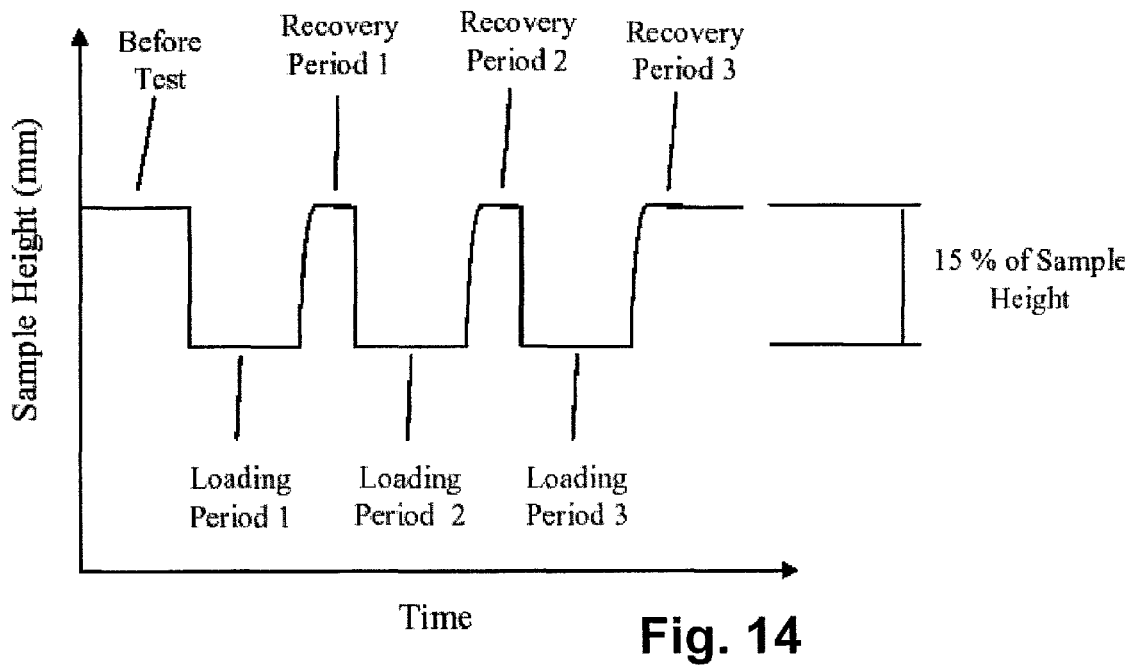
FIG. 14 illustrates the results of a representative test of the stress relaxation properties of the hydrogel of the invention.

Stress Relaxation:

A 12 mm diameter material test specimen 8 mm in height is placed in a 37° C. bath of an isotonic aqueous solution. A stress relaxation study is performed on the specimen consisting of 15% displacement for 16 hours followed by 8 hours of unloaded recovery. The sample is tested through three successive cycles. Mass and modulus values are calculated before and after the three-cycle test. A plot of the conditions imposed in a typical testing cycle is presented in FIG. 14. The embodiment of the fully hydrated hydrogel as prepared in Example 1 shows less than 5% change in mass, modulus, and water content under this stress relaxation protocol.

Figure 15:
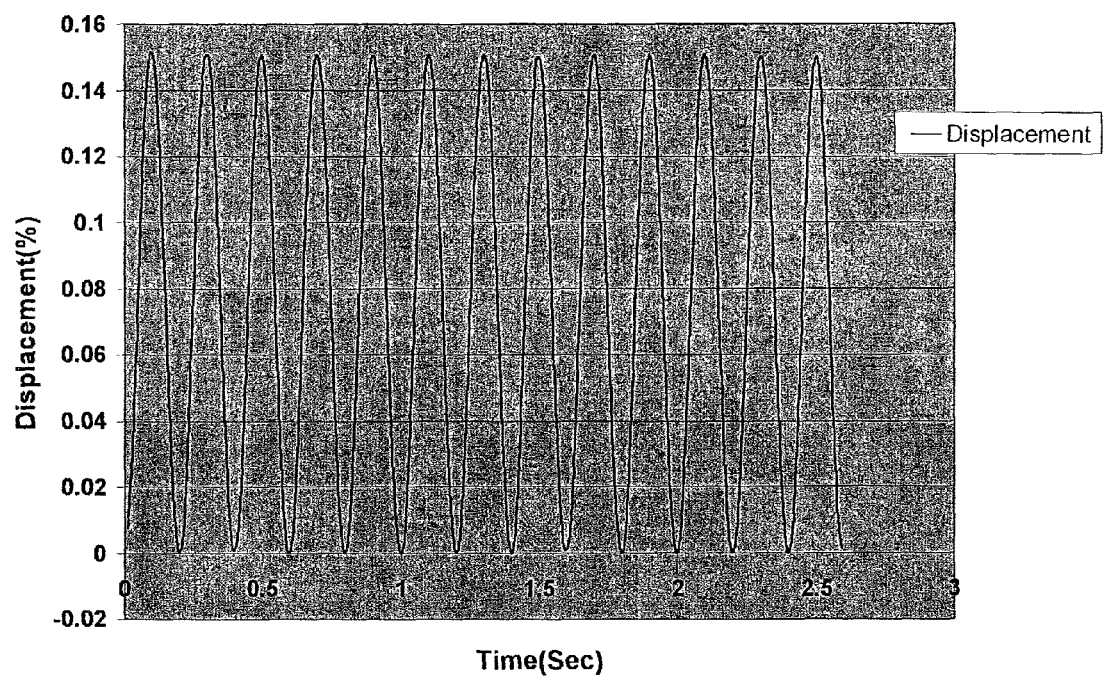
FIG. 15 illustrates the fatigue testing conditions for the hydrogel of the invention.

Fatigue:

A fatigue study is performed to test for changes in water content under physiologic loading in the following manner. A 12 mm diameter test specimen 8 mm in height is weighed measured and tested to determine compressive incremental modulus values. The sample is placed in a bath of an isotonic aqueous solution at 37° C. and then cycled through 0-15% displacement for 1 million cycles at a frequency of 5 Hz, as shown in FIG. 15. After cyclic testing, the test specimen is again weighed, measured, and incremental modulus value calculated. The embodiment of the fully hydrated hydrogel as prepared in Example 1 shows less than 5% change in mass, modulus, and water content under this fatigue protocol.

EXAMPLE 4

This example illustrates restoration of the mechanical properties of a spinal motion segment using a physiologically fully hydrated hydrogel prosthesis in accordance with the invention.

Figure 16:
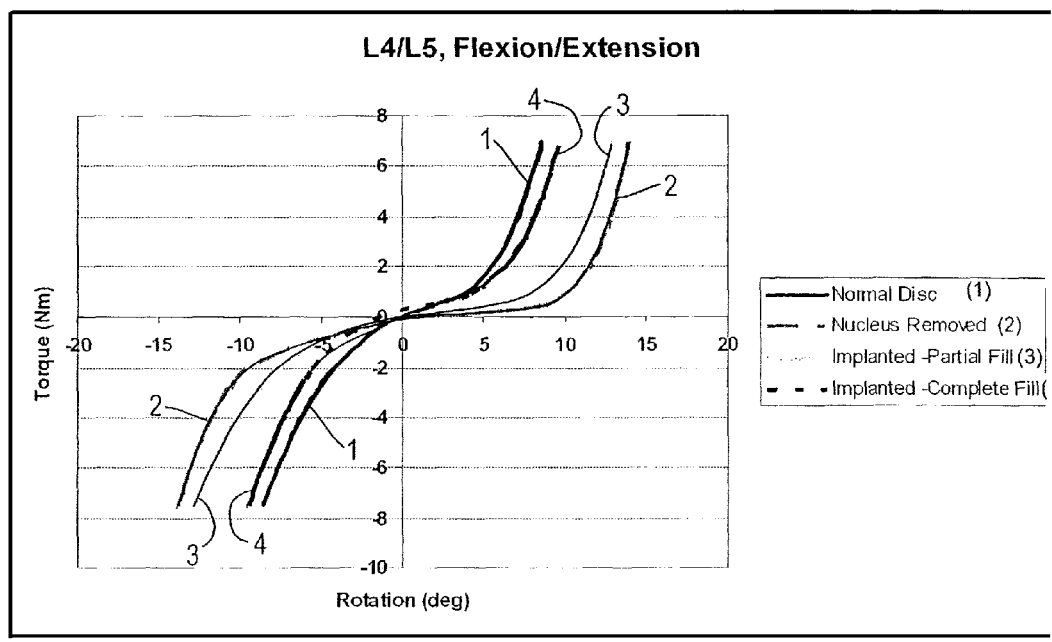
FIG. 16 illustrates the results of mechanical measurements on a spinal motion segment having a hydrogel implant according to the invention.

A flexibility experiment was conducted by performing the process of the invention for replacing the nucleus pulposus, and measuring the flexibility of the intervertebral unit at various steps to simulate the degeneration and restoration of the nucleus. An appropriate specimen of an L4/L5 spinal motion segment was selected, including the L4 and L5 lumbar vertebrae and the intervertebral disc therebetween with intact annulus fibrosus and nucleus pulposus. The selected specimen had an essentially normal nucleus pulposus. The specimen was subjected to measurement of flexibility at four stages before, during and after the nucleus replacement procedure by conducting a simulated flexion-extension series using pure moments. The torque required for a range of defined angles of flexion and extension was applied. The results are presented in the chart in FIG. 16.

The first of the four flexion-extension series was conducted on the intact healthy disc; the results are shown in Curve 1. The nucleus was then removed and the specimen was tested through the same applied moments as shown in Curve 2. Accordingly, the second series simulates a severely degraded nucleus. The specimen was then implanted with a physiologically fully hydrated hydrogel implant of the invention, equilibrated using an isotonic saline solution, that partially filled the core and was tested again, thereby simulating a somewhat degenerated nucleus or a nucleus replaced without pressurization. The implant comprised a physiologically fully hydrated hydrogel having a diameter of about 3 mm and was inserted through the vertebral endplate. A length of about 120 mm of implant was used. A movement towards normal physiologic values over the range of motion was found, shown in Curve 3. Finally, when the specimen was implanted with a physiologically hydrated hydrogel implant of the invention (about 3 diameter and about 120 mm in length) and the core was completely filled and pressurized, using the technique described above, close to full restoration of the disc mechanics was found, as shown in Curve 4.

The method of the invention using the physiologically fully hydrated hydrogel of the invention provides the clinician with a number of advantages. The amount of hydrogel to be implanted can be predetermined and in order to achieve a desired volume of implant with a resulting stable dimension of the implant. The method of implantation provides appropriate feedback through direct monitoring of the pain response of the patient to avoid overpressurization of the disc nucleus cavity or to detect a situation wherein the intervertebral disc is chemically sensitive. Furthermore, by using an embodiment of the physiologically substantially fully hydrated hydrogel containing a radiopaque material, e.g., $BaSO_4$, it is possible to monitor the implantation through interactive radiographic and/or fluoroscopic visualization.

The method of the invention using a physiologically fully hydrated hydrogel also provides flexibility in the surgical intervention by reason of its ability to readily accommodate variations in anatomy of a patient and variations in the size and/or shape of the intervertebral disc cavity due to varied effectiveness in nucleus removal. It provides the option of full nucleus replacement or partial nucleus replacement (through partial removal of the nucleus), or augmentation of the nucleus by simply adding implant without previously removing nucleus material.

The prosthesis and method of the invention are well adapted:
to fill variably-shaped nucleus cavities;
to provide for volumetric filling without requiring a large entrance or insertion opening into the nucleus cavity;
to provide for varied volumetric filling by allowing for arbitrarily variable lengths of polymer to be inserted;
to minimize the possibility of subsequent implant expulsion by providing a relatively small cross-sectional area of the insertion opening and minimizing probability that the end of the implant could be positioned at the insertion opening in the annulus fibrosis and thereby escape from the pulposus cavity through the insertion opening.

The invention having been described in the foregoing, it will be apparent to those skilled in the art that many variations and/or changes can be made therein without departing from the nature and spirit of the invention, and all such changes and/or variations are intended to be included within the scope of the invention.

What is claimed is:

1. A method of replacing or supplementing a nucleus pulposus of an intervertebral disk, comprising the steps of:
providing a solid hydrogel body;
hydrating the hydrogel body in an isotonic aqueous solution so that the hydrogel body is substantially osmotically balanced with the targeted nucleus pulposus; and
inserting the hydrated hydrogel body into the intervertebral disk by a minimally invasive surgical procedure to replace or supplement the nucleus pulposus, the hydrogel body having a ratio of length to principal transverse dimension not less than about 5:1.

2. The method of claim 1, wherein the isotonic aqueous solution is dextran.

3. The method of claim 1, wherein the hydrogel body has a ratio of length to principal transverse dimension of about 350:1.

4. The method of claim 1, wherein the hydrogel body has an elastic modulus not greater than about 4 megapascals.

5. The method of claim 1, wherein the hydrogel body has an elastic modulus between about 0.05 megapascals and about 4.0 megapascals.

6. The method of claim 1, wherein the hydrogel body has a generally cylindrical shape.

7. The method of claim 1, wherein the hydrogel body has at least one portion with a cross-sectional area greater than a principal cross-sectional area of said body.

8. The method of claim 1, wherein the hydrogel body has at least one end provided with a terminal portion of transverse cross-sectional area greater than a principal cross-sectional area of said body.

9. The method of claim 1, wherein the hydrogel body has at least one end provided with a flared terminal portion of transverse cross-sectional area greater than a principal cross-sectional area of said body.

10. The method of claim 1, wherein the hydrogel body has at least one end provided with a generally spherical terminal portion of transverse cross-sectional area greater than a principal cross-sectional area of said body.

11. The method of claim 1, wherein the hydrogel body has at least one portion between its ends with a transverse cross-sectional area greater than a principal cross-sectional area of said body.

12. The method of claim 1, wherein the hydrogel body is capable of folding upon itself to physiologically fill a central region of an annulus fibrosus.

13. The method of claim 1, wherein the hydrogel body comprises a polyvinyl alcohol copolymer.

14. The method of claim 1, wherein the hydrogel body comprises a copolymer of polyvinyl alcohol and poly(vinylpyrrolidone).

15. The method of claim 1, wherein the hydrogel body comprises a mixture of poly(vinyl alcohol) and poly(vinyl pyrrolidone).

16. The method of claim 1, wherein the hydrogel body comprises a radiopaque material.

17. The method of claim 16, wherein the radiopaque material is barium sulfate.

18. The method of claim 1, wherein the hydrogel body has a ratio of length to principal transverse dimension of about 40:1.

19. The method of claim 1, wherein the hydrogel body has a ratio of length to principal transverse dimension of about 100:1.

20. The method of claim 1, wherein the hydrogel body has a ratio of length to principal transverse dimension of about 200:1.

* * * * *